United States Patent [19]

DeCastro et al.

[11] Patent Number: 5,188,955
[45] Date of Patent: Feb. 23, 1993

[54] METHOD OF PRESERVING ARYLACYLAMIDASE IN AQUEOUS SOLUTION

[75] Inventors: Aurora F. DeCastro, Union, Mich.; Surendra K. Gupta, Elkhart; Steven M. Shantz, Goshen, both of Ind.

[73] Assignee: GDS Technology, Inc., Elkhart, Ind.

[21] Appl. No.: 823,452

[22] Filed: Jan. 21, 1992

Related U.S. Application Data

[63] Continuation-in-part of Ser. No. 596,794, Oct. 11, 1990, abandoned, which is a continuation-in-part of Ser. No. 116,169, Oct. 28, 1987, Pat. No. 4,999,288.

[51] Int. Cl.$^5$ ............................ C12N 9/96; C12N 9/78
[52] U.S. Cl. ..................................... 435/188; 435/227; 435/187
[58] Field of Search ......................... 435/188, 227, 187

[56] References Cited

U.S. PATENT DOCUMENTS

| | | | |
|---|---|---|---|
| 4,310,625 | 1/1982 | Modrovich | 435/15 |
| 4,414,327 | 11/1983 | Hammond et al. | 435/877 |
| 4,430,433 | 2/1984 | Hammond et al. | 435/877 |
| 4,675,296 | 6/1987 | Lehmussaari et al. | 435/188 |
| 4,764,468 | 8/1988 | Wehner et al. | 435/188 |
| 4,999,288 | 3/1991 | de Castro et al. | 435/18 |

Primary Examiner—David M. Naff
Assistant Examiner—Mike Meller
Attorney, Agent, or Firm—Browdy & Neimark

[57] ABSTRACT

Arylacylamidase can be stabilized by inhibiting conformational changes using either o-cresol or benzoic acid or salts of benzoic acid as a stabilizing agent. The compositions show significantly enhanced stability of arylacylamidase in aqueous solution, lyophilized, and solid-phase formats.

11 Claims, No Drawings

METHOD OF PRESERVING ARYLACYLAMIDASE IN AQUEOUS SOLUTION

The present application is a continuation-in-part of application Ser. No. 07/596,794, filed Oct. 11, 1990, now abandoned which is a continuation in part of application Ser. No. 07/116,169, filed Oct. 28, 1987, now U.S. Pat. No. 4,999,288, both of which are hereby incorporated by reference in their entirety.

FIELD OF THE INVENTION

The present invention relates to methods for preserving arylacylamidase compositions during storage.

BACKGROUND OF THE INVENTION

Arylacylamidase E.C., 3.5.1.13. has been isolated from various microbial organisms, such as *Pseudomonas acidovorans* (ATCC 15668) by J. Alt et al., in *J. Gen. Microb.* 87: 260 (1975) and in *Eur. J. Biochem.* 53: 357 (1975); *Bacillus schaericus* (ATCC 12123) by G. Englehart et al.; *Pseudomonas fluorescens* (ATCC 39005) and *Pseudomonas putida* (ATCC 39004) by Hammond et al., U.S. Pat. No. 4,414,327.

Arylacylamidases from different microorganisms have been used in the determination of anilides such as acetaminophen by Hammond et al. in *Anal. Biochem.* 143: 152 (1984) and in U.S. Pat. No. 4,999,288.

However, it has recently been estimated that a great many of all in vitro diagnostic tests conducted annually in this country are not reliable. Unreliable tests can result in unnecessary medical treatment, the withholding of unnecessary treatment, and incorrect treatment. Because of their high specificity, the use of enzyme determinations has significantly increased during the last few years, and indications are that this trend will continue. However, rigorous quality control measures are required to assure the accuracy and consistency of results. This requirement stems in part from the fact that the exact nature of enzymes, as well as the mechanisms of their action, remain unknown for the most part. At present, the greatest limitation on the use of enzymes lies in the unstable characteristics of the enzymes themselves. Current methodologies require the use of numerous labile ingredients.

The present commercial state of the art for stabilizing the reactive ability of enzymes is by locking them into a solid matrix either by freeze drying, dry blending such as used for tableting dried powders, primarily in the pharmaceutical diagnostic and related industries, and immobilization by locking the chemical structure of the enzyme into a solid matrix. Contrary to the sophistication these terms imply, these approaches are neither practical nor desirable, and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending, and the usefulness of the product is further limited by packaging modes and sizes. It is far more convenient for the ultimate user to obtain the enzyme in solution, as it is in this form that the enzyme is most readily used,.

Arylacylamidases in particular are very delicate and highly susceptible to loss in activity. These enzymes are not stable in either aqueous or lyophilized form, and thus it would be particularly useful to provide a stable arylacylamidase composition which has a reasonably long shelf life at ambient temperatures.

A number of prior art workers have attempted to stabilize a variety of enzymes, among them the arylacylamidases, with varying degrees of success. For example, Modrovich, in U.S. Pat. No. 4,310,625, discloses a method for stabilizing labile enzymes by forming a solution of the enzyme in an aqueous medium containing at least 20% organic solvent in the presence of a small amount of polymer such as gelatin. The stability can be further enhanced by including from 1-18% of salts and a bacteriostatic agent to prevent degradation of the substrate, which may serve as food for bacteria, fungi and other microorganism. None of the enzymes stabilized by this method is an arylacylamidase, and the stabilizing is effected by protecting the functional group site of the enzyme.

Hammond, in U.S. Pat. No. 4,414,327, discloses a process for preserving arylacylamidases in aqueous solution by including glycerol in the solution. The glycerol is present in amounts of from 10 to 70% glycerol volume/volume. In order further to retain the activity of the enzyme, the enzyme solution is stored at low temperatures (5 to $-20°$ C.).

SUMMARY OF THE INVENTION

It is an object of the present invention to overcome the aforementioned deficiencies in the prior art.

It is another object of the present invention to provide a stable form of arylacylamidase.

It is yet another object of the present invention to provide a stable form of arylacylamidase that can be stored at ambient temperatures.

It is a further object of the present invention to provide a stable form of arylacylamidase which is stabilized by inhibiting conformational changes in the enzyme.

According to the present invention, conformational changes in arylacylamidase are prevented by dissolving the arylacylamidase in a medium consisting essentially of water and optional buffer materials with an effective amount of a stabilizing agent selected from the group consisting of o-cresol, benzoic acid and salts thereof, and mixtures of o-cresol and benzoic acid or benzoic acid salts. Because o-cresol in concentrations above about 0.5% specifically destabilizes arylacylamidase, it is important to maintain the concentration of o-cresol below about 0.5% in the presence of arylacylamidase. No organic solvent is present in the composition according to the present invention, and there is no need for an enzyme substrate in the composition.

The enzyme activity of a protein is determined by the spatial arrangement of the amino acids in its polypeptide chains. The maintenance of the correct "conformation" of the protein is necessary for its activity. Processes such as dissolution of the enzyme in solution or buffers, lyophilization, drying of the enzyme into a solid matrix such as paper or polymer in a test device, or environmental factors such as temperature, often affect the desired enzyme conformation adversely and denature the protein. This causes a loss in enzyme activity, which can seriously affect any assays conducted with the enzyme. Therefor, it is advantageous to provide a method for maintaining the conformation of the enzyme and thus maintain its full activity.

Generally, compounds which are structurally similar to the enzyme substrate bind to the enzyme but cannot be successfully used to stabilize the enzyme because either they themselves act as a substrate or become inhibitors to the enzyme. Surprisingly, it has been found in the present invention that compounds such as benzoic acid and o-cresol, which have some structural similarity to anilides such as acetaminophen, act to stabilize arylacylamidase and that, furthermore, neither compound is used by the enzyme as a substrate nor causes inhibition of the activity of arylacylamidase. The stability of arylacylamidase is very critical because it allows the preparation of a stable test composition in liquid or solid-phase format for use in assays, including electrochemical methods, which can be used for the determination of anilides such as acetaminophen. Moreover, a stable composition containing the arylacylamidase enzyme is very useful because it can be stored for a predetermined length of time so that it need not be acquired fresh each time it is to be used.

Ortho-cresol has previously been used as a separate reagent for the purpose of color development in the estimation of anilides in chemical methods a shown in *Ann. Clin. Biochem.* 6: 81 (1969) and *Ann. Clin. Biochem.* 13: 435 (1976) as well as enzymatic methods in U.K. Patent No. 2,089,978 and U.S. Pat. No. 4,414,327. In these publications, o-cresol in concentrations of about 1% was used so that it chemically combined with the hydrolysis product of the anilide to be determined to produce a colored compound. However, there is no disclosure or suggestion in any of these publications that o-cresol could affect the stability of arylacylamidase. Moreover, it has been found that concentrations of o-cresol of above about 0.5% act to destabilize the arylacylamidase enzyme, so that it was particularly surprising to discover that low concentrations of o-cresol could act as stabilizers for the enzyme.

Benzoic acid as well as its salts, such as sodium and potassium benzoate, has previously been used as a preservative or bactericidal agent. However, this compound has never been shown to be a stabilizer for the enzyme arylacylamidase.

The stabilized arylacylamidase compositions of the present invention consist essentially of the arylacylamidase per se and the stabilizing agent, either o-cresol, benzoic acid or a salt thereof, or a mixture of o-cresol and benzoic acid or a salt thereof. When the enzyme is prepared in lyophilized form, for example, as an impregnant for filter paper strips, there is no need for additional ingredients other than optional buffer. When the enzyme composition is in liquid form, it is generally dissolved in water along with the stabilizing agent and optional buffer. The aqueous solutions are generally maintained at a pH of from about 5.0 to about 9.0 by means of suitable buffers, including Tris.HCl or borate buffer. As will be appreciated by one skilled in the art, other conventional buffers for enzyme solutions can be used.

DETAILED DESCRIPTION OF THE INVENTION

The superior storability and stability of arylacylamidase compositions of the present invention will be evident from the following nonlimiting examples. In each of the examples, the arylacylamidase enzyme E.C. 3.5.1.13. was obtained from GDS Technology, Inc. of Elkhart, Ind.

EXAMPLE 1

This example illustrates the stabilizing effect of o-cresol on arylacylamidase. At pH 8.0, over 80% activity of an aqueous solution of arylacylamidase was maintained even after 14 days at 37° C. in the presence of 2.8 mM o-cresol, whereas only 15% activity was left in a similar aqueous solution which contained no o-cresol.

Arylacylamidase enzyme was dissolved in water containing 50 mM borate buffer at various pH's at widely different concentrations of between 1 and 1500 U/L in the presence of between 1 and 12 mM o-cresol. The same solution of enzyme in buffer was prepared without o-cresol. Both sets of solutions were maintained at 37° C. for a period of two weeks. The enzyme activity was measured at the beginning of the period, as well as at certain times during the two week period. The enzyme activity was determined by a method which uses 50 mM Tris.HCl, pH 8.5, and 1 mM paranitroacetanilide as the enzyme substrate. In the presence of arylacylamidase, the p.nitroacetanilide is hydrolyzed to p-nitroaniline which absorbs at 405 nm. The kinetic assay was performed at 30° C. and 405 nm. One unit of enzyme activity is defined as 1 $\mu$ mole of p.nitroaniline formed using p-nitroacetanilide as a substrate at 30° C. Table 1 illustrates the stabilizing effect of o-cresol on the enzyme activity.

TABLE 1

REMAINING ENZYME ACTIVITY IN U/ML AT 37° C.

| CON-DITION | TIME | | | | |
|---|---|---|---|---|---|
| | 0 HRS | 5 HRS | 3 DAYS | 7 DAYS | 14 DAYS |
| pH 8.0, No o-cresol | 13.5 | 12.9 | 9.44 | 4.71 | 1.87 |
| pH 8.0, 2.8 mM o-cresol | 13.6 | 13.5 | 13.6 | 12.3 | 11.8 |
| pH 8.0, No o-cresol | 6.26 | 5.81 | 4.15 | 2.01 | 0.85 |
| pH 8.0, 4.2 mM o-cresol | 6.25 | 6.16 | 6.20 | 5.66 | 5.36 |
| pH 9.0, No o-cresol | 13.6 | 5.09 | 0.06 | 0 | 0 |
| pH 9.0, 2.2 mM o-cresol | 13.6 | 13.7 | 11.2 | 9.26 | 5.44 |
| pH 9.0, No o-cresol | 6.16 | 2.27 | 0 | 0 | 0 |
| pH 9.0, 3.75 mM o-cresol | 6.15 | 6.20 | 5.03 | 4.16 | 2.36 |

EXAMPLE 2

Two arylacylamidase aqueous solutions of 100 U/L were prepared in water containing 50 mM borate buffer, pH 8.0, one in the presence of 10 mM o-cresol and one in the absence of o-cresol. Whatman 54 and Whatman 3MM paper strips (2"×12") were impregnated with these solutions and dried. The dried paper strips were stored at 37° C. for two weeks. At the end of the two week period, the strips were examined or tested by extracting the enzyme activity from the paper by shaking for ten minutes in 10 mL borate buffer in water. The enzyme activity was measured using the assay described in Example 1.

The results of this experiment are shown in Table 2

TABLE 2

| Sample of Arylacylamidase | O-cresol 10 mM | Residual Activity (Recovery) |
|---|---|---|
| Strips of Whatman 54 | YES | 70% |
| Strips of Whatman 54 | NO | 20% |
| Strips of Whatman 3 MM | YES | 40% |

TABLE 2-continued

| Sample of Arylacylamidase | O-cresol 10 mM | Residual Activity (Recovery) |
|---|---|---|
| Strips of Whatman 3 MM | NO | 0% |

This example clearly demonstrates that o-cresol has a strong stabilizing effect on arylacylamidase compositions when incorporated in a solid matrix, which can be used in tests that measure anilides either colorimetrically or electrochemically.

EXAMPLE 3

This example represents the stabilizing ability that sodium benzoate has on lyophilized arylacylamidase.

An aqueous solutiOn of arylacylamidase, from about 100-200 U/mL, in 10 mM Tris-HCl buffer, which was maintained at pH 7.0, was lyophilized in the presence of various amounts of sodium benzoate and in the absence of sodium benzoate. After lyophilization, the enzyme samples were dissolved in deionized water to make an aqueous enzyme solution of 100 U/mL of water, and assayed for enzyme activity using the assay described in Example 1.

Table 3 shows the % of enzyme recovery after lyophilization, demonstrating the stabilizing effect of sodium benzoate on the enzyme during the lyophilization process.

TABLE 3

| Compounds added to the enzyme preparation | % Recovery After Lyophilization |
|---|---|
| 0 mM sodium benzoate | <50 |
| 1 mM sodium benzoate | 75 |
| 5 mM sodium benzoate | 95 |
| 10 mM sodium benzoate | 104 |

EXAMPLE 4

Example 4 illustrates the stabilizing effects of sodium benzoate or benzoic acid in aqueous solutions of arylacylamidase at a variety of temperatures. The arylacylamidase was dissolved in an aqueous buffer, such as in 10 mM Tris-HCl, pH 7.0, in the presence of 1 mg/ml sodium benzoate and in the absence of sodium benzoate.

The samples were maintained at 4° C., room temperature, and 37° C. The residual activity was determined using the enzyme assay described in Example 1.

TABLE 4

| | Remaining Activity at 4° C. (8 days) | Remaining Activity at Room Temp (8 days) | Remaining Activity at 37° C. | |
|---|---|---|---|---|
| | | | (1 day) | (4 days) |
| Arylacylamidase 24.3 U/mL | 55% | 5% | 0% | 0% |
| Arylacylamidase 21.6 U/mL with 1 mg/mL sodium benzoate | 80% | 71% | 85% | 30% |

This example further illustrates that the enzyme in the presence of sodium benzoate was more stable at all temperatures tested than the control sample without sodium benzoate. Similar results were obtained with 50 mM phosphate buffer at pH 6.0.

EXAMPLE 5

Example 5 illustrates the stabilizing effect of sodium benzoate and benzoic acid on arylacylamidase in solid form. In this instance, the arylacylamidase was impregnated into a fibrous substrate, such as filter paper, and dried.

Arylacylamidase aqueous solutions of 150 U/mL were prepared with water, 50 mM borate buffer, and with 10 mM sodium benzoate or in the absence of sodium benzoate. Whatman 54 and Whatman 3MM paper strips (2"×12") were impregnated with each solution and dried. The dried strips were stored at 37° C. for two weeks. Two weeks later, the strips were examined and tested for enzyme activity. The enzyme was extracted from the paper strips by shaking in 10 mL borate buffer for 30 minutes. The enzyme activity was measured using the assay described in Example 1.

TABLE 5

| Sample of Arylacylamidase | Sodium Benzoate 10 mM | Residual Activity (Recovery) |
|---|---|---|
| Strips of Whatman 54 | YES | 85% |
| Strips of Whatman 54 | NO | 24% |
| Strips of Whatman 3 MM | YES | 70% |
| Strips of Whatman 3 MM | NO | <5% |

This clearly demonstrates that sodium benzoate has a stabilizing effect on arylacylamidase compositions when incorporated in a solid-phase matrix.

EXAMPLE 6

An aqueous solution of arylacylamidase enzyme at the concentration of 3.5 U/ml was made which contained 0.1 mM sodium benzoate and 3.75 mM o-cresol. The aqueous solution of 3.5 U/ml arylacylamidase was prepared without O-cresol and sodium benzoate. Both solutions were maintained at 37° C. for two weeks. The enzyme activity was measured at the beginning of the period, as well as at the two week period. The enzyme activity was determined using the assay method described in Example 1. Table 6 illustrates the stabilizing effect of O-cresol and sodium benzoate as a mixture on the enzyme activity.

TABLE 6

| Remaining Enzyme activity in U/ML at 38° C. | | |
|---|---|---|
| Conditions | 0 hr | 14 days |
| Enzyme No benzoate and no o-cresol | 3.5 | 0 |
| Enzyme with benzoate and o-cresol | 3.5 | 3.2-3.5 |

The arylacylamidase enzyme converts an anilide to aniline or aniline derivatives. In the case of acetaminophen, arylacylamidase converts the anilide to 4.hydroxyaniline The 4-hydroxyaniline can then react with a phenol derivative, such as ortho-cresol, to produce color.

The arylacylamidase enzyme E.C. 3.5.1.13 used in e present invention was obtained from GDS TECHNOLOGY, INC, Elkhart, Ind. The enzyme was isolated from a Gram positive organism other than Pseudomonas sp. and was obtained in a lyophilized form free from glycerol.

It is necessary that the amount of stabilizer, either benzoic acid or ortho-cresol, be carefully controlled. For example, it was found that 10-100 mg/ml of ortho-cresol enhances the stability of the enzyme. This is in contrast to previously used higher concentrations of ortho-cresol, on the order of about 1%, which were described in U.K. Patent 2089978 and U.S. Pat. No. 4,414,327. These high concentrations of of ortho-cresol inactivate the enzyme and make it unstable.

Importantly and unexpectedly, it has also been found that the same amount of ortho-cresol necessary for the stabilization of the enzyme is sufficient to allow the color reaction to take place simultaneously with the enzymatic reaction, thus greatly simplifying the determination. Phenol and other phenol derivatives such as guaiacol can be used to produce color with 4-hydroxyaniline, but at a slower rate. Although sodium benzoate and benzoic acid also stabilize the arylacylamidase, these compounds do not develop color in the presence of an aniline. In such instances, color producing compounds such as ortho-cresol or phenol derivatives may be included in the the reagent composition when a test is conducted. However, the enzyme compositions can contain both benzoic acid or a benzoic acid salt along with o-cresol in an amount which is not sufficient to destabilize the enzyme. Preferably, the o-cresol is present in amounts less than about 0.5%, even in the presence of benzoic acid or a benzoate.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A method for inhibiting conformational changes in arylacylamidase E.C. 3.5.1.13 consisting essentially of adding to an aqueous solution of said arylacylamidase E.C. 3.5.1.13 wherein the solution consists essentially of water and said arylacylamidase an effective amount to inhibit conformational changes of said arylacylamidase of a stabilizing agent having a phenyl group selected from the group consisting of o-cresol, benzoic acid, salts of benzoic acid, and mixtures thereof.

2. The method according to claim 1 wherein the stabilizing agent is o-cresol.

3. The method according to claim 2 wherein said o-cresol is present in an amount of from about 0.1 mM to about 10 mM.

4. The method according to claim 1 wherein the stabilizing agent is selected from the group consisting of benzoic acid and salts of benzoic acid.

5. The method according to claim 1 wherein said benzoic acid or benzoate salts are present in an amount of from about 0.1 mM to about 100 mM.

6. The method according to claim 1 wherein the stabilizing agent is a mixture of benzoic acid and o-cresol.

7. The method according to claim 1 wherein a fibrous. substrate is impregnated with the resulting solution containing arylacylamidase and stabilizng agent.

8. The method according to claim 7 wherein said fibrous substrate is filter paper.

9. The method according to claim 1 wherein said aqueous solution has a pH ranging from about 6.0 to about 9.5.

10. The method according to claim 9 wherein said aqueous solution further includes a buffer.

11. The method according to claim 1 wherein said aqueous solution is lyophilized after the stabilizing agent is added to the solution.

* * * * *